US011253173B1

(12) United States Patent
Demiralp

(10) Patent No.: US 11,253,173 B1
(45) Date of Patent: Feb. 22, 2022

(54) DIGITAL CHARACTERIZATION OF MOVEMENT TO DETECT AND MONITOR DISORDERS

(71) Applicant: Verily Life Sciences LLC, Mountain View, CA (US)

(72) Inventor: Emre Demiralp, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 456 days.

(21) Appl. No.: 15/992,938

(22) Filed: May 30, 2018

Related U.S. Application Data

(60) Provisional application No. 62/512,620, filed on May 30, 2017.

(51) Int. Cl.
*A61B 5/00* (2006.01)
*A61B 5/11* (2006.01)
*G16H 50/50* (2018.01)

(52) U.S. Cl.
CPC .......... *A61B 5/1127* (2013.01); *A61B 5/1114* (2013.01); *A61B 5/1122* (2013.01); *G16H 50/50* (2018.01)

(58) Field of Classification Search
CPC ........ G16H 50/20; G16H 50/70; G16H 50/50; G16H 10/60; G16H 15/00; G16H 20/10; G16H 30/40; G16H 50/30; A61B 2505/07; A61B 5/00; A61B 5/1118; A61B 5/68; A61B 5/6802; A61B 5/4023; A61B 5/4088; A61B 5/4836; A61B 5/7264; A61B 5/1127; A61B 5/1122; A61B 5/1114

USPC .................. 600/300, 587, 595, 424; 702/160
See application file for complete search history.

(56) References Cited

U.S. PATENT DOCUMENTS

| | | | |
|---|---|---|---|
| 5,919,149 A * | 7/1999 | Allum | A61B 5/1116 600/595 |
| 6,231,577 B1 | 5/2001 | Canedy | |
| 6,383,150 B1 * | 5/2002 | Stewart | A61B 5/4023 600/300 |
| 6,876,947 B1 * | 4/2005 | Darley | A43B 3/0078 702/160 |
| 8,398,560 B2 * | 3/2013 | Elser | A61B 7/003 600/534 |
| 8,626,472 B2 * | 1/2014 | Solinsky | A61B 5/4076 702/160 |
| 8,628,485 B2 * | 1/2014 | Wilson | A61B 5/743 600/592 |
| 8,771,206 B2 * | 7/2014 | Gettelman | A61B 34/10 600/587 |
| 8,821,416 B2 * | 9/2014 | Johansson | A61B 5/0024 600/587 |

(Continued)

*Primary Examiner* — May A Abouelela
(74) *Attorney, Agent, or Firm* — Perkins Coie LLP

(57) ABSTRACT

Introduced here are techniques for digitally characterizing the movement of a subject in order to detect the presence of a disorder or monitor the progression of the disorder. More specifically, one or more angular features can be identified that define how certain part(s) of the human body move relative to other part(s) of the human body. These angular feature(s) can be used, for example, to affirmatively diagnose instances of a disorder, eliminate a disorder as the source of symptoms experienced by a subject, generate confidence scores that can be used to assist in diagnosing a subject, monitor disorder progression due to treatment or lack thereof, etc.

20 Claims, 17 Drawing Sheets

(56) References Cited

U.S. PATENT DOCUMENTS

| | | | |
|---|---|---|---|
| 8,961,439 B2* | 2/2015 | Yang | A61B 5/1038 600/595 |
| 9,165,113 B2* | 10/2015 | Greene | G06F 19/00 |
| 9,524,424 B2* | 12/2016 | Greene | A61B 5/112 |
| 9,782,122 B1* | 10/2017 | Pulliam | A61B 5/1112 |
| 10,427,293 B2* | 10/2019 | Asbeck | B25J 9/0006 |
| 10,485,454 B2* | 11/2019 | Tas | A61B 5/7246 |
| 10,716,495 B1* | 7/2020 | Romrell | A61B 5/681 |
| 10,755,817 B2* | 8/2020 | Mariottini | G16H 50/20 |
| 2002/0060633 A1* | 5/2002 | Crisco, III | A61B 5/1121 340/669 |
| 2002/0062067 A1* | 5/2002 | Casper | A61B 5/16 600/300 |
| 2003/0139692 A1* | 7/2003 | Barrey | A61B 5/061 600/595 |
| 2008/0146968 A1 | 6/2008 | Hanawaka et al. | |
| 2008/0152192 A1* | 6/2008 | Zhu | G06K 9/209 382/103 |
| 2008/0221487 A1* | 9/2008 | Zohar | A61B 5/224 600/595 |
| 2009/0030350 A1 | 1/2009 | Yang et al. | |
| 2009/0204031 A1* | 8/2009 | McNames | A61B 5/1126 600/595 |
| 2010/0042011 A1* | 2/2010 | Doidge | G06T 17/10 600/544 |
| 2010/0191100 A1* | 7/2010 | Anderson | G06F 19/3481 600/424 |
| 2011/0052005 A1* | 3/2011 | Selner | A61B 5/7264 382/103 |
| 2011/0245633 A1* | 10/2011 | Goldberg | A61B 5/165 600/301 |
| 2012/0232430 A1* | 9/2012 | Boissy | A61B 5/1118 600/595 |
| 2013/0170129 A1 | 7/2013 | Sullivan | |
| 2014/0206667 A1* | 7/2014 | Gallagher | A61K 31/496 514/211.13 |
| 2014/0228712 A1* | 8/2014 | Elliott | A63B 71/06 600/587 |
| 2014/0303508 A1* | 10/2014 | Plotnik-Peleg | G06F 19/00 600/483 |
| 2014/0309692 A1 | 10/2014 | Mor et al. | |
| 2015/0208975 A1* | 7/2015 | Ghajar | G16H 20/70 600/595 |
| 2016/0015972 A1* | 1/2016 | Hyde | A61B 5/1127 607/48 |
| 2016/0030391 A1* | 2/2016 | Gallagher | A61P 25/28 514/424 |
| 2016/0147959 A1* | 5/2016 | Mariottini | G16H 50/20 706/46 |
| 2016/0166180 A1* | 6/2016 | Martin | A61B 5/4866 702/141 |
| 2016/0180050 A1* | 6/2016 | Holmes | G16H 50/30 705/3 |
| 2016/0198998 A1* | 7/2016 | Rahimi | A61B 5/1127 600/595 |
| 2016/0202755 A1* | 7/2016 | Connor | A61B 5/1126 73/865.4 |
| 2016/0302696 A1 | 10/2016 | Wilson et al. | |
| 2016/0338644 A1* | 11/2016 | Connor | A61B 5/1071 |
| 2017/0007168 A1* | 1/2017 | Mirelman | A61B 5/7278 |
| 2017/0095667 A1* | 4/2017 | Yakovlev | A61N 1/0553 |
| 2017/0156662 A1* | 6/2017 | Goodall | A61B 5/0036 |
| 2017/0202724 A1* | 7/2017 | De Rossi | A61B 5/6811 |
| 2017/0231532 A1* | 8/2017 | Chakravarty | A61B 5/1128 600/595 |
| 2017/0231569 A1* | 8/2017 | Kumar | A61B 5/6829 600/476 |
| 2017/0243354 A1* | 8/2017 | Tafazzoli | A61B 5/7275 |
| 2017/0258390 A1* | 9/2017 | Howard | A61B 5/4803 |
| 2017/0273601 A1* | 9/2017 | Wang | A61B 5/4833 |
| 2017/0287146 A1* | 10/2017 | Pathak | G06T 7/0016 |
| 2017/0293805 A1* | 10/2017 | Kontschieder | G16H 50/20 |
| 2017/0344706 A1* | 11/2017 | Torres | G16H 40/20 |
| 2018/0031374 A1* | 2/2018 | Hepler | G01C 21/16 |
| 2018/0070875 A1* | 3/2018 | Kshetrapal | A61B 5/1118 |
| 2018/0330058 A1* | 11/2018 | Bates | G16H 10/60 |
| 2018/0360349 A9* | 12/2018 | Dohrmann | A61B 5/1036 |
| 2019/0298253 A1* | 10/2019 | Hal | A61B 5/1128 |

* cited by examiner

800

801
Import movement data

802
Identify angular feature(s) defined by markers

803
Run analysis of variance (ANOVA) on the identified angular feature(s)

804
Determine F-statistic for each identified angular feature

805
Identify angular features having high F-statistics as candidates for disorder metrics

901 Acquire movement data

902 Parse the movement data and identify angular feature(s)

903 Analyze values associated with the angular feature(s)

904 Render a diagnoses of a disorder if appropriate

FIGURE 9

DIGITAL CHARACTERIZATION OF MOVEMENT TO DETECT AND MONITOR DISORDERS

CROSS-REFERENCE TO RELATED APPLICATIONS

This application claims priority to U.S. Provisional Application No. 62/512,620, titled "Digital Characterization of Movement to Detect and Monitor Disorders" and filed on May 30, 2017, which is incorporated by reference herein in its entirety.

TECHNICAL FIELD

Various embodiments concern techniques for digitally characterizing the movement of human bodies to stratify individuals suffering from movement disorders and/or musculoskeletal disorders.

BACKGROUND

Movement disorders can be defined as neurologic syndromes with either an excess of movement or a paucity of voluntary/involuntary movements. Examples of movement disorders include Parkinson's disease and multiple sclerosis (MS). Musculoskeletal disorders, meanwhile, can be defined as conditions that impact the musculoskeletal system (e.g., muscles, tendons, ligaments, nerves, or blood vessels) and affect the movement of a human body. Examples of musculoskeletal disorders include tendonitis, osteoporosis, rheumatoid arthritis, and traumas (e.g., sprains and joint replacement).

Diagnoses of movement disorders and musculoskeletal disorders are typically made by a medical professional (e.g., a neurologist, podiatrist, or physiatrist) who observes a subject and then renders a diagnosis of a particular disorder. But these diagnoses can be difficult to make with high accuracy. For example, accurate diagnoses require the medical professional have knowledge of the full range of disorders. Proper evaluation of disorder progression can be difficult for similar reasons. For example, individuals suffering from a disorder may exhibit different (i.e., heterogeneous) symptoms or similar (i.e., homogeneous) symptoms of differing intensity.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 8 depicts a flow diagram of a process for performing an angular feature search.

FIG. 9 depicts a flow diagram of a process for rendering a diagnosis of a disorder.

Figures 1A, 1B:
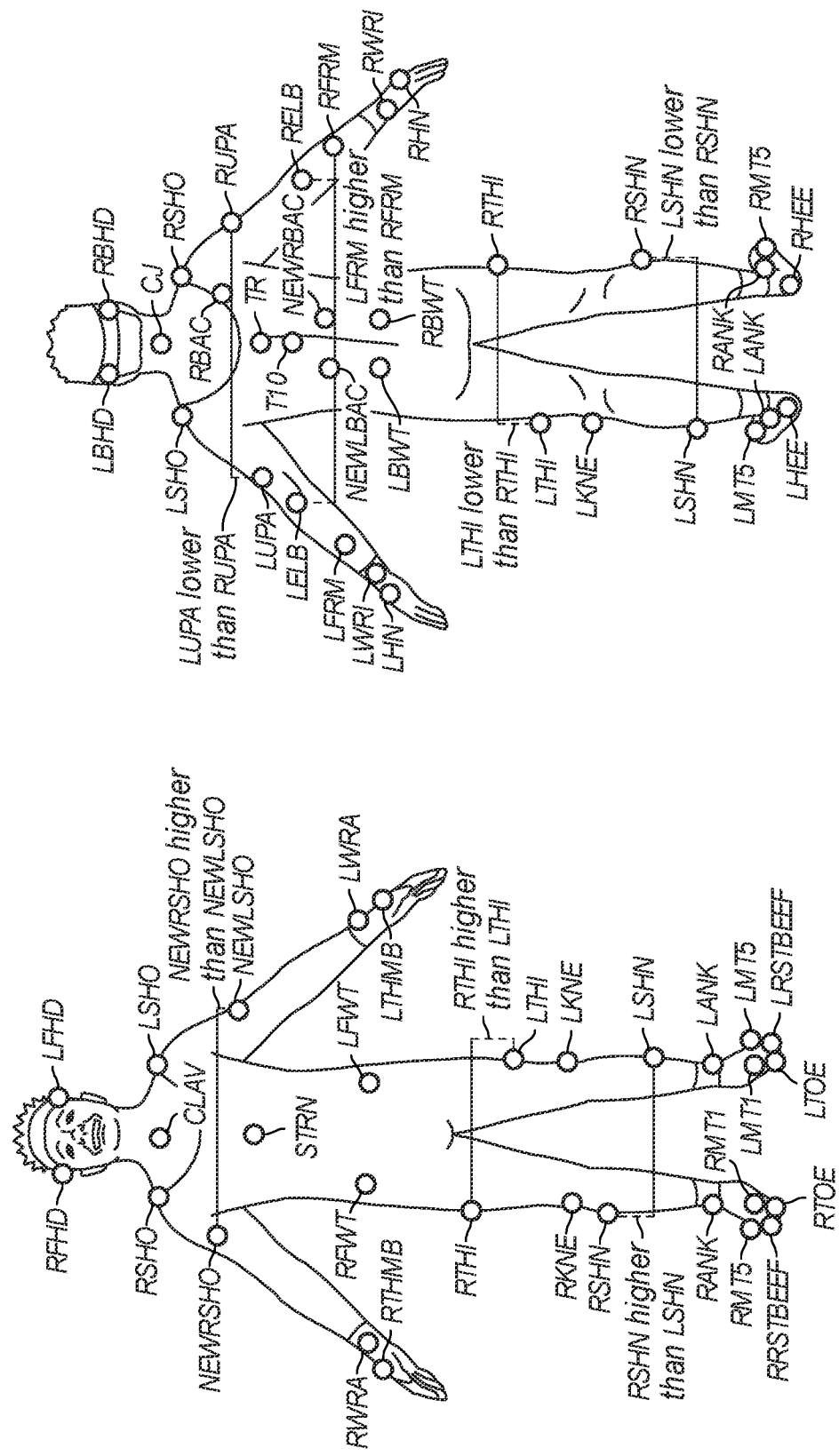
FIG. 1A depicts a frontal view of a human body on which an arrangement of markers is located.
FIG. 1B depicts a rear view of a human body on which an arrangement of markers is located.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Quantitative measures can be used to diagnose neurological motor disorders, joint disorders, musculoskeletal disorders, or other movement dysfunctions (collectively referred to as "movement disorders" or simply "disorders" for brevity), monitor disorder progression, etc. For example, some diagnostic processes use an analysis of static quantitative metrics such as posture, strength, or movement, while other diagnostic processes require an analysis of simple first-order representations of body position such as knee angle, lordosis, and kyphosis. However, these quantitative measures do not always capture how the movements of different parts of the human body are related.

Motion capture (e.g., via a camera, a wearable motion sensor, etc.) represents an alternative to these quantitative measures. While motion capture technology enables movement to be accurately tracked (e.g., by creating a digital character that represents a subject), the positional information that is naturally derived by the motion capture technology generally is not sufficient for characterizing dynamic, higher-order phenomena that incorporate positional information corresponding to multiple points along a living human body. For example, the positional information generated by a motion capture technology cannot be used to identify granular features that are useful in characterizing a disorder and its progression.

Introduced here, therefore, are techniques for digitally characterizing the movement of human bodies to stratify subjects who may be suffering from a disorder. More specifically, one or more angular features can be identified that define how certain part(s) of a human body move relative to other part(s) of the human body. These angular feature(s) could be used, for example, to affirmatively diagnose instances of a disorder, eliminate a disorder as the source of symptoms experienced by a subject (i.e., to negatively diagnose instances of the disorder), generate confidence scores that can be used to assist in diagnosing a subject, monitor disorder progression due to treatment or lack thereof, etc.

For example, some embodiments pertain to a computer-implemented technique that includes identifying the movement of markers affixed to a living human body captured while the human body performs a known activity (e.g., walking, running, crouching, or jumping), determining a first set of angular samples from the identified movement, and determining a second set of angular samples from the identified movement. Each marker may correspond to a different location on a predetermined structure of a population of human bodies. Said another way, each marker may be associated with a structure that is substantially consistent across a population of human bodies so that movement of a human body (or a portion thereof) can be ready tracked for the purpose of detecting/diagnosing movement disorders. For example, markers may be arranged proximate to the toes, ankle, shin, knee, and/or hip of each leg to detect the presence of a movement disorder affecting movement of the lower body. As another example, markers may be arranged proximate to the thumb, wrist, elbow, bicep, and/or shoulder of each arm to detect the presence of a movement disorder affecting movement of the lower body. As further described below, markers could also be arranged across the entire body to determine how these different structures move with respect to one another (e.g., how the left leg moves in relation to the right leg, how the legs move in relation to the torso, shoulders, or head, etc.).

The first set of angular samples may correspond to the relative positions of a first set of multiple markers, while the second set of angular samples may correspond to the relative positions of a second set of multiple markers. The first and second sets of multiple markers may at least partially differ from one another (i.e., at least one marker is not shared between the sets in some embodiments). Each angular sample in the first set may temporally correspond to an angular sample in the second set. When movement of the markers is monitored over a time interval, separate temporally aligned data sets may be produced for the first and second sets of multiple markers.

Moreover, each angular sample in the first set and corresponding angular sample in the second set may form a point in a multi-dimensional angular distribution. By examining the values in the multi-dimensional angular distribution, a computing device can determine whether the relationship between the first set of multiple markers and the second set of multiple markers has changed. For example, if the first set of multiple markers defines left knee angle and the second set of multiple markers defines right knee angle, examination of the multi-dimension angular distribution will enable the discover of changes in the relationship between the left knee angle and the right knee angle.

Accordingly, the computer-implemented technique may also include discovering a geometric pattern of points in the multi-dimensional angular distribution, and determining a movement disorder diagnostic based on the geometric pattern. More specifically, the discovered geometric pattern in the multi-dimensional angular distribution can be compared to a source geometric pattern known to represent confirmed cases of a movement disorder. The comparison may be done visually, programmatically (e.g., comparing values one-by-one), etc. For example, an interface may include a first plot of the source geometric pattern and a second plot of the discovered geometric pattern. By examining these plots, an individual (e.g., a medical professional, such as a physician or nurse) can determine whether there is significant variation in the relationship between the first set of multiple markers and the second set of multiple markers. As another example, individual points in the discovered geometric pattern can be compared with corresponding points in the source geometric pattern. For instance, an interface may include the highest value in each geometric pattern, the lowest value in each geometric pattern, the average (e.g., mean and/or median) value in each geometric pattern, etc.

Although some embodiments may be described in the context of certain types of motion capture technology (e.g., inertial sensors such as accelerometers, gyroscopes, etc.), the technology described herein is generally source-agnostic. That is, movement data can be analyzed regardless of whether it originates from a professional motion capture environment, an in-clinic motion capture environment, or a free living (e.g., home) environment.

Embodiments may also be described with reference to particular system configurations and networks. However, those skilled in the art will recognize that the features described herein are equally applicable to other system configurations, network types, etc. Moreover, the technology can be embodied as special-purpose hardware (e.g., circuitry), programmable circuitry appropriately programmed with software and/or firmware, or as a combination of special-purpose and programmable circuitry. Accordingly, embodiments may include a machine-readable medium having instructions that may be used to program a computing device to perform a process for parsing movement data to detect the presence of motion abnormalities indicative of a disorder, monitor the progression of a disorder, etc.

Embodiments may be described with reference to particular computer programs, system configurations, networks, etc. However, those skilled in the art will recognize that these features are equally applicable to other computer program types, system configurations, network types, etc. For example, while an embodiment may be described in the context of a certain type of inertial sensor, those skilled in the art will recognize that the relevant feature is equally applicable when using another type of inertial sensor.

Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for parsing movement data to detect the presence of motion abnormalities indicative of a disorder, render an affirmative diagnosis of a disorder, monitor the progression of a disorder, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

Motion capture (also referred to as "motion tracking") is the process of recording the movement of a subject. The subject wears markers that are tracked in order to identify movements based on the positions of certain markers or the angles between certain markers. Several different types of motion capture exist.

Passive Markers—Passive markers are coated with a retroreflective material that reflects light generated near the lens of a camera used to monitor the subject. Passive markers are usually attached directly to the subject's skin or clothing.

Active Markers—Positions of the subject are triangulated by simultaneously or sequentially illuminating different active markers (e.g., light-emitting diodes) in order to identify individual active markers by their relative positions. Rather than reflect light back toward a camera, active markers are powered and emit their own light.

Virtual Markers—Special computer algorithms are designed to analyze multiple streams of optical input, identify human forms, and break each human form down into constituent parts for tracking. Emerging techniques have led to the rapid development of virtual markers, which do not require that subjects wear special equipment for tracking.

Inertial—Inertial sensors (also referred to as "inertial measurement units") are attached to the subject. Inertial sensors generate movement data that may specify force, angular rate, magnetic field, etc. The movement data is typically wirelessly transmitted to a computing device, where posture and motion can be analyzed.

While the term "markers" may be used to describe certain embodiments, those skilled in the art will recognize that any type of motion capture can be used. For example, some embodiments use inertial sensors or virtual marker technology rather than passive markers or active markers to generate movement data indicative of subject movement. Accordingly, the technology introduced here may be source-agnostic so long as movement data is made available for review.

Figure 1C:
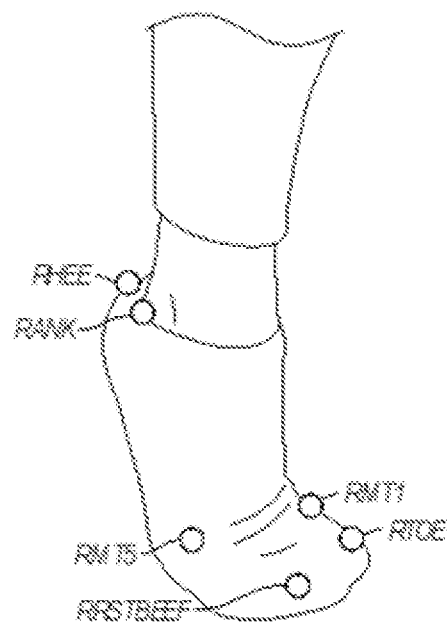
FIG. 1C depicts a perspective view of a foot on which an arrangement of markers is located.
Figure 1D:
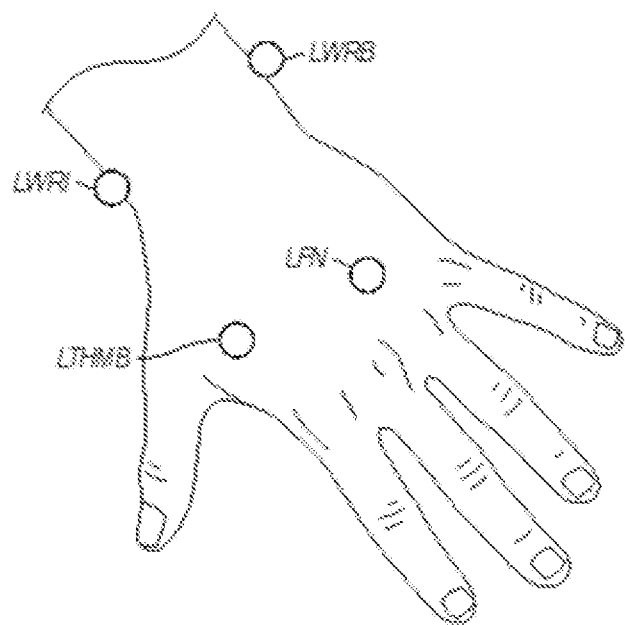
FIG. 1D depicts a top view of a hand on which an arrangement of markers is located.

FIGS. 1A-D depict an arrangement of markers that may be used in some embodiments. FIGS. 1A-B depict frontal and rear views, respectively, of a human body on which the arrangement of markers is located. FIG. 1C depicts a perspective view of a foot on which an arrangement of markers is located, while FIG. 1D depicts a top view of a hand on which an arrangement of markers is located.

As further described below, any combination of these markers could be used while monitoring the movement of a subject. In some embodiments the movement of each marker shown in FIG. 1A is monitored, while in other embodiments only a subset of these markers is monitored. For example, a computing device (e.g., a mobile phone, laptop computer, or computer server) may only examine movement data associated with the markers located below the waist, above the waist, etc. In such embodiments, the computing device may filter movement data associated with other markers that are not presently of interest (e.g., those on the arms, head, etc.).

Table I includes short descriptions of some markers that are shown in FIGS. 1A-D. Some embodiments of the technology monitor other markers in addition to, or instead of, those listed in Table I.

TABLE I

Short descriptions of markers shown in FIGS. 1A-D.

| Marker Identifier | Body Part Descriptor |
|---|---|
| RFHD | Right Front Head |
| LFHD | Left Front Head |
| RBHD | Right Back Head |
| LBHD | Left Back Head |
| RSHO | Right Top Shoulder |
| LSHO | Left Top Shoulder |
| CLAV | Midpoint Between Clavicles |
| C7 | C7 Vertebra |
| STRN | Midpoint of Sternum |
| RBAC | Right Scapula |
| T8 | T8 Vertebra |
| T10 | T10 Vertebra |
| NEWLBAC | Left Latissiumus Dorsi |
| NEWRBAC | Right Latissiumus Dorsi |
| RFWT | Right Front Hip |
| LFWT | Left Front Hip |

TABLE I-continued

Short descriptions of markers shown in FIGS. 1A-D.

| Marker Identifier | Body Part Descriptor |
|---|---|
| RBWT | Right Rear Hip |
| LBWT | Left Rear Hip |
| NEWRSHO | Right Front Shoulder |
| NEWLSHO | Left Front Shoulder |
| RWRA | Right Radial-Side Wrist |
| LWRA | Left Radial-Side Wrist |
| RTHMB | Right Thumb |
| LTHMB | Left Thumb |
| LUPA | Left Upper Arm |
| RUPA | Right Upper Arm |
| LELB | Left Elbow |
| RELB | Right Elbow |
| LFRM | Left Forearm |
| RFRM | Right Forearm |
| LWRB | Left Ulnar-Side Wrist |
| RWRB | Right Ulnar-Side Wrist |
| LFIN | Left Index Finger |
| RFIN | Right Index Finger |
| RTHI | Right Thigh |
| LTHI | Left Thigh |
| RKNE | Right Knee |
| LKNE | Left Knee |
| RSHN | Right Shin |
| LSHN | Left Shin |
| RANK | Right Ankle |
| LANK | Left Ankle |
| RMT5 | Fifth Digit Right Foot |
| LMT5 | Fifth Digit Left Foot |
| RMT1 | First Digit Right Foot |
| LMT1 | First Digit Left Foot |
| RRSTBEEF | . . . |
| LRSTBEEF | . . . |
| RTOE | . . . |
| LTOE|$_{[PAT(1]}$ | . . . |
| RHEE | Right Heel |
| LHEE | Left Heel |

Figure 2A:
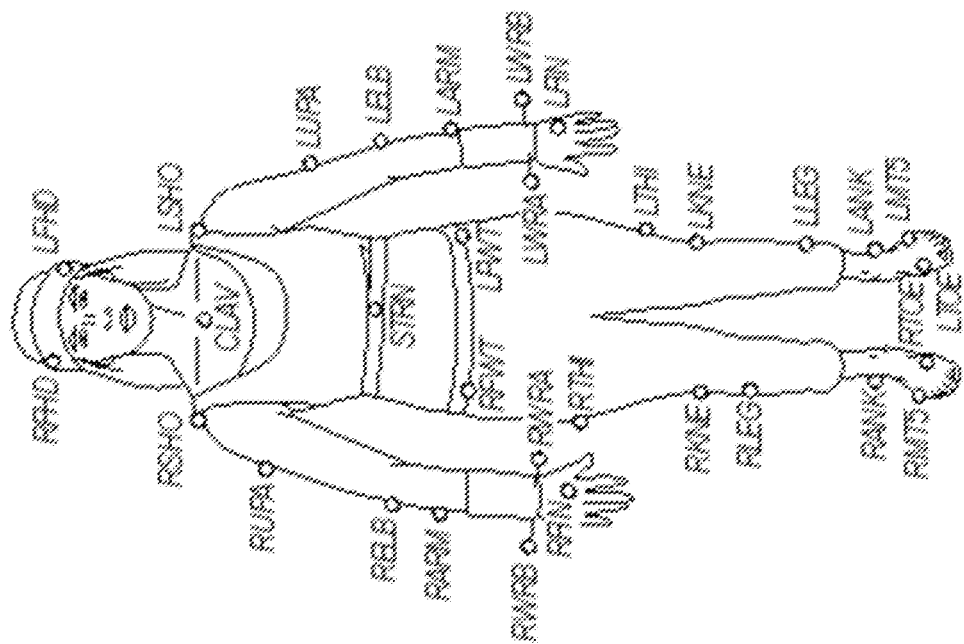
FIG. 2A depicts a rear view of a human body on which an arrangement of markers is located.
Figure 2B:
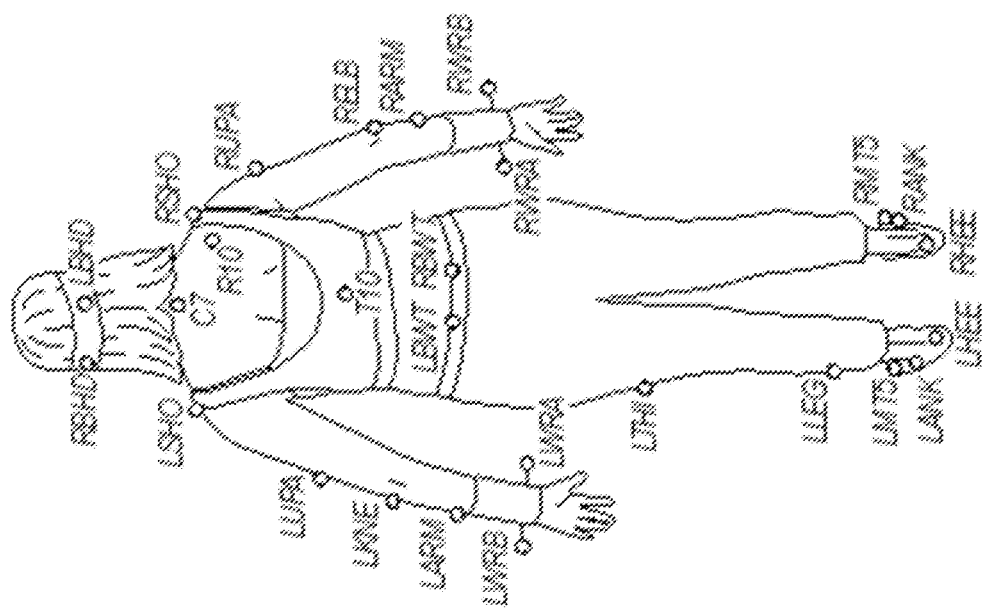
FIG. 2B depicts a frontal view of a human body on which an arrangement of markers is located.
Figure 2D:
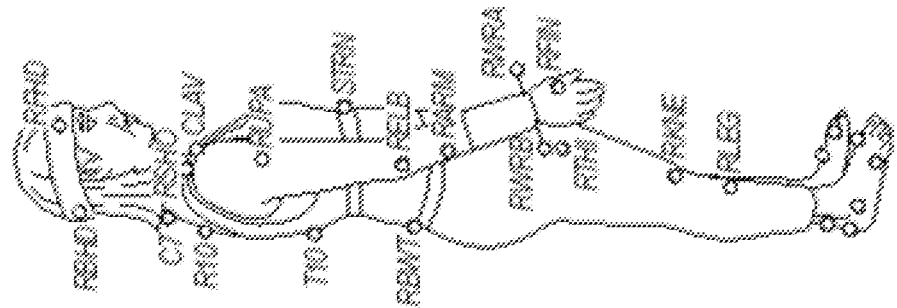
FIG. 2D depicts a right-side view of a human body on which an arrangement of markers is located.
Figure 2C:
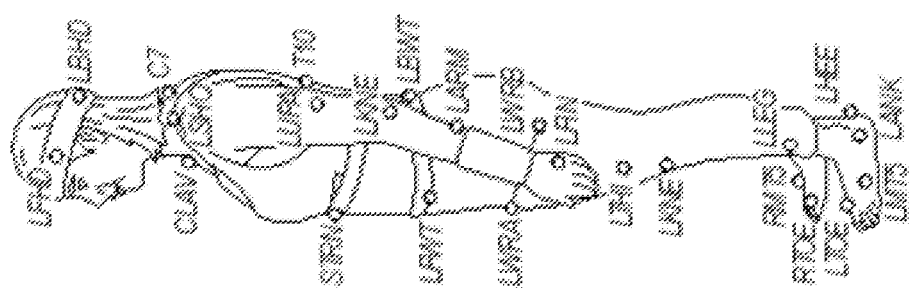
FIG. 2C depicts a left-side view of a human body on which an arrangement of markers is located.

FIGS. 2A-D depict another arrangement of markers that may be used in some embodiments. FIGS. 2A-B depict rear and frontal views, respectively, of a human body on which the arrangement of markers is located, while FIGS. 2C-D depict left- and right-side views, respectively, of the human body on which the arrangement of markers is located. Some or all of these markers could be tracked to better understand the movement of a subject.

Certain combinations of these markers define angular features that can be monitored over time. Therefore, an "angular feature" characterizes the angular relationship between a certain set of markers that are tracked by motion capture technology. Accordingly, the value of an angular feature can be defined by the positions of at least three markers (e.g., one marker that acts as a pivot point, and two markers that respectively represent the ends of branches extending from the pivot point) at a given point in time. For example, the markers STRN, LBWT, and LFWT may define the lower pelvic angle, while the markers STRN, LBWT, and T10 may define the upper pelvic angle. Other angular features can be defined by the positions of at least two markers. For example, the markers T10 and C7 may define the upper back angle, while the markers RSHO and LSHO may define the shoulder plane.

Several factors influence which of these markers are used. For example, most or all of the markers can be tracked on a subject having a disorder whose biomechanics are not well known, such as cerebral palsy or multiple sclerosis (MS). Conversely, fewer markers may be tracked on a subject who has recently suffered a trauma (e.g., a sprain or a broken bone) because there is greater understanding of the biomechanics associated with traumas.

Thus, one factor may be the current understanding regarding the disorder being diagnosed or monitored. Generally, a larger number of markers is desirable for those disorders whose biomechanics are not well known. However, if the source of the disorder is known (such as in the case of traumas), a more targeted approach may be employed where multiple markers are affixed to the relevant area. For example, more than three markers may be affixed to the left leg if the subject has recently undergone knee replacement surgery. In order to increase the resolution of the motion capture technology responsible for monitoring movement, the number of markers affixed within/near a given area can be increased.

Another factor may be limitations imposed by the motion capture technology or the processing technology responsible for parsing the movement data generated by the motion capture technology. For example, a professional motion capture environment may enable all of the markers shown in FIGS. 1A-D or FIGS. 2A-D to be tracked in real time, while an in-clinic motion capture environment may only allow a subset of those markers to be tracked in real time.

As noted above, other forms of motion capture technology could also be used to monitor the movement of a subject. For example, one or more inertial sensors (or some other form of motion sensor) may be used to track the movement of the subject outside of a clinic environment, where the subject is more likely to advertently or inadvertently influence the results. The inertial sensor(s) could be affixed to or embedded within an article of clothing (e.g., a shirt, pair of pants, shoe, or wearable device such as a watch), an isolated calibration platform, etc. Accordingly, movement data could be generated within a professional motion capture environment, an in-clinic motion capture environment, a free living (e.g., home) environment, or any combination thereof.

Introduced here are techniques for digitally characterizing the movement of a subject based on movement data. More specifically, validated angular features can be identified that relate to established outcomes across different disorders, such as tuberculosis (TB), MS, Parkinson's disease, cerebral palsy, etc. More specifically, by examining the movement of multiple subjects afflicted with a disorder, a specific set of validated angular feature(s) could be identified that is indicative of the disorder. The specific set of validated angular feature(s) may be referred to as a "metric" for detecting the presence or progression of the disorder. Accordingly, a disorder could be affirmative diagnosed by monitoring the validated angular feature(s) that define the metric corresponding to the disorder.

Different metrics may be used to diagnose the presence of a single ailment.

Figure 3B:
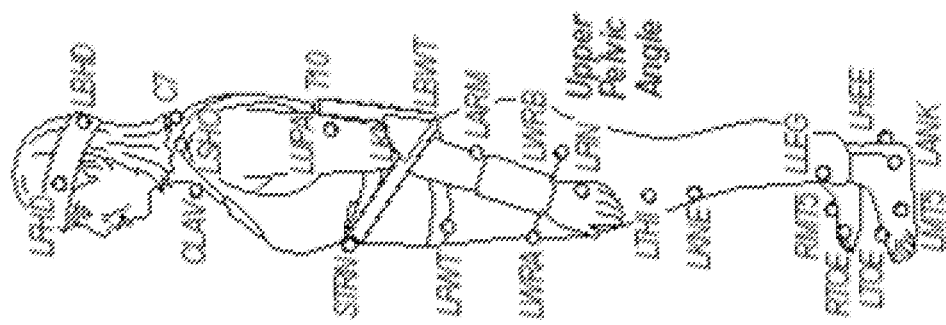
FIG. 3B illustrates an upper pelvic angle that can be used to diagnose cases of pregnancy.
Figure 3A:
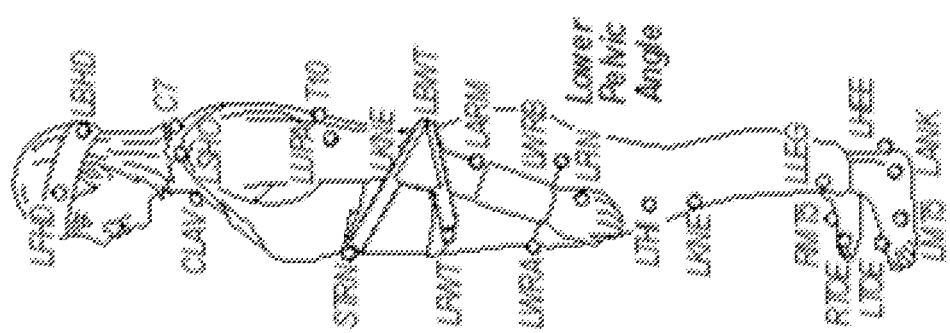
FIG. 3A illustrates a lower pelvic angle that can be used to diagnose cases of pregnancy.
Figure 3D:
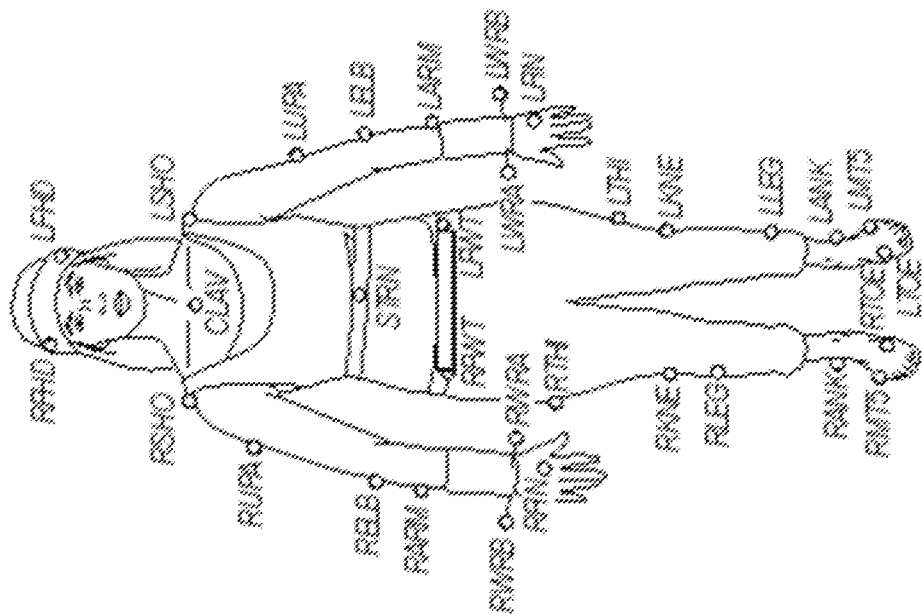
FIG. 3D illustrates pelvic angle as can be seen from a frontal view of a human body.
Figure 3C:
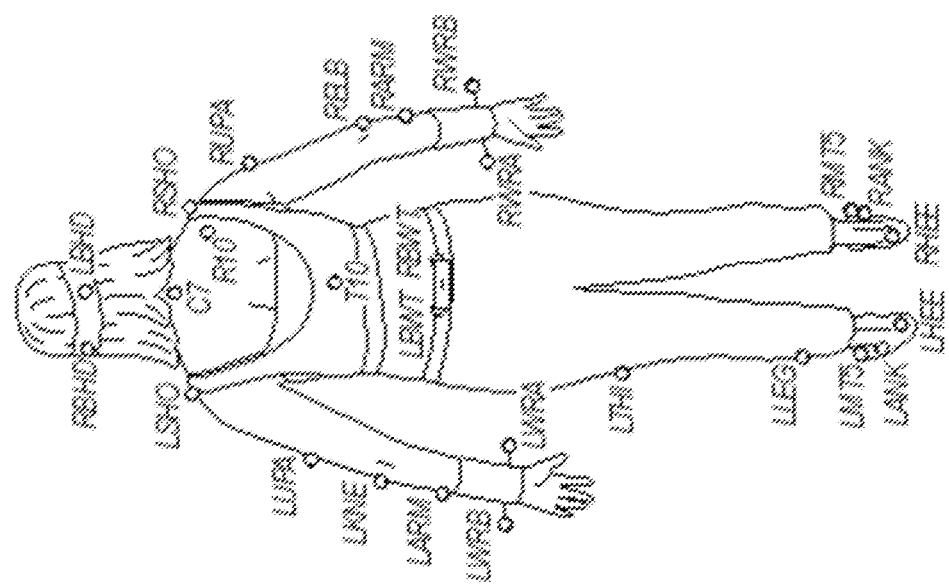
FIG. 3C illustrates pelvic angle as can be seen from a rear view of a human body.

For example, FIGS. 3A-D illustrate how the lower pelvic angle and the upper pelvic angle could be used to diagnose cases of pregnancy. More specifically, FIGS. 3A-B illustrate a lower and upper pelvic angle, respectively, while FIGS. 3C-D illustrate pelvic angle as can be seen from a rear and frontal view, respectively. By monitoring the positions of the appropriate markers, a computing device can readily detect minor variations in the value of these angular features.

FIGS. 4A-B, FIGS. 5A-C, and FIGS. 6A-C depict other angular features that can also be used to diagnose cases of pregnancy. Each of these angular features is defined by a different subset of markers.

Figure 4B:
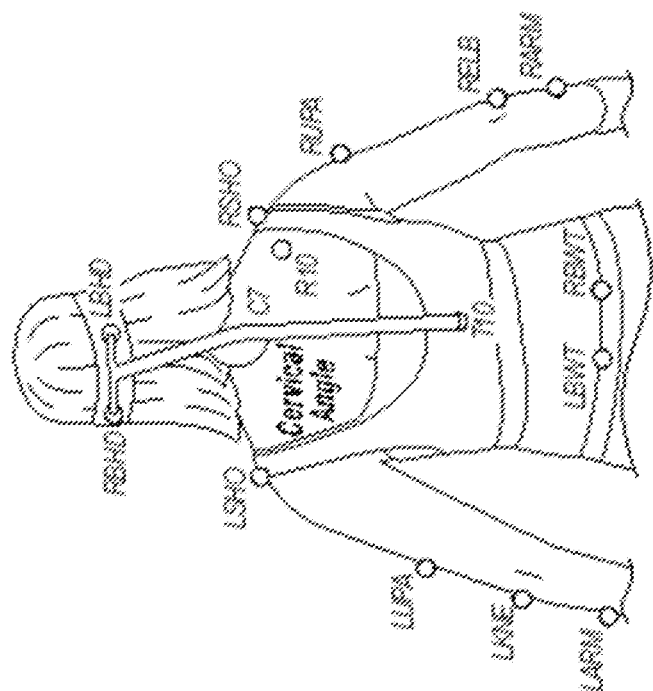
FIG. 4B illustrates thoracic angle as can be seen from a rear view of a human body.
Figure 4A:
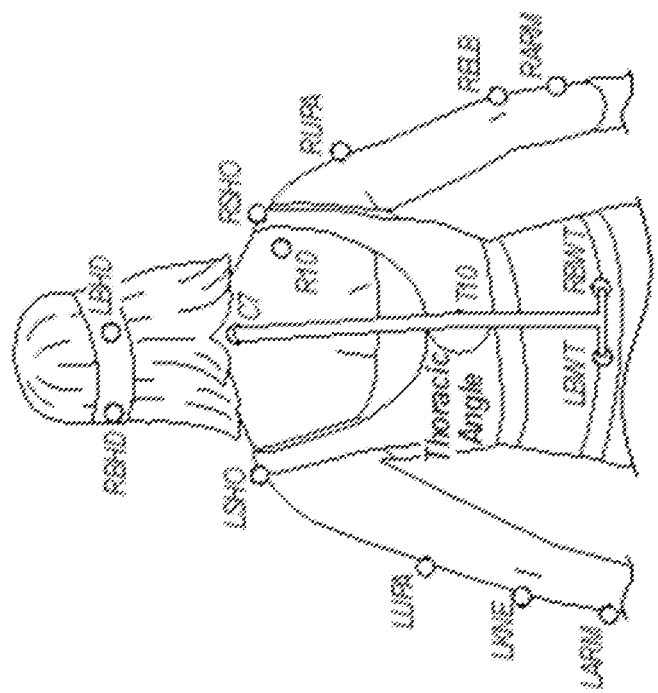
FIG. 4A illustrates cervical angle as can be seen from a rear view of a human body.

FIG. 4A-B illustrate how the cervical angle and the thoracic angle of a subject can be readily monitored. The cervical angle may be defined by T10, C7, and the midpoint between RBHD and LBHD, while the thoracic angle may be defined by C7, T10, and the midpoint between LBWT and RBWT. Some angular features are defined based on spatial proximity to a marker. Here, for example, the cervical angle is defined based on a location (i.e., the midpoint between RBHC and LBHD) that does not directly correspond to a marker. Instead, the location is defined with respect to at least one marker.

Figure 5B:
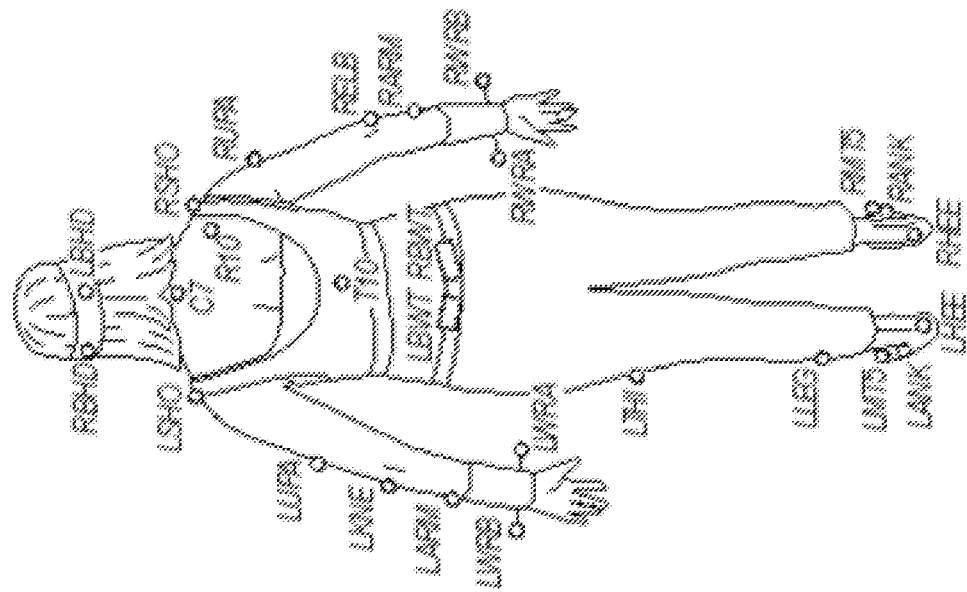
FIG. 5B illustrates left and right hip angles as can be seen from a rear view of a human body.
Figure 5A:
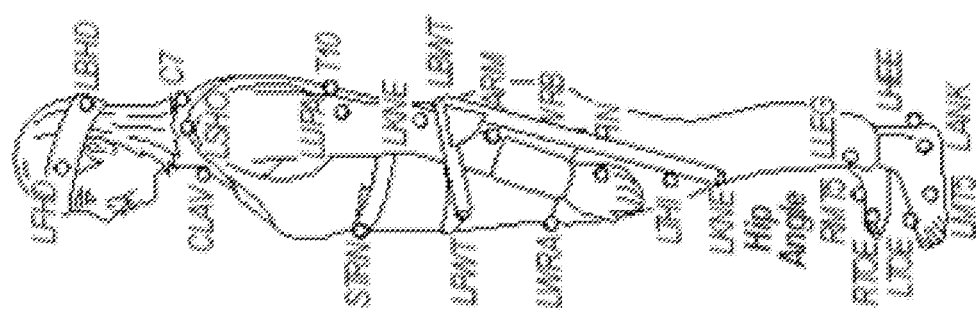
FIG. 5A illustrates left hip angle as can be seen from a left-side view of a human body.
Figure 5C:
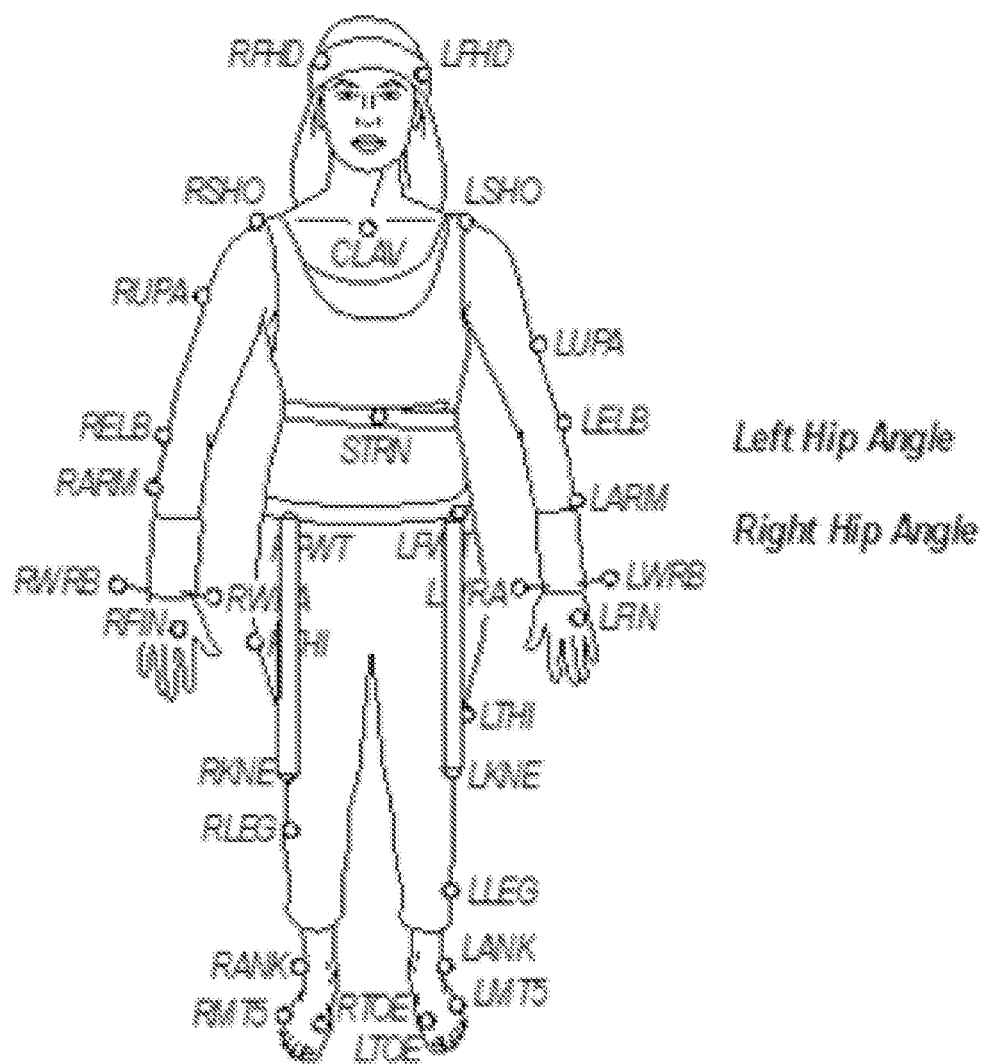
FIG. 5C illustrates left and right hip angles as can be seen from a frontal view of a human body.
Figure 6B:
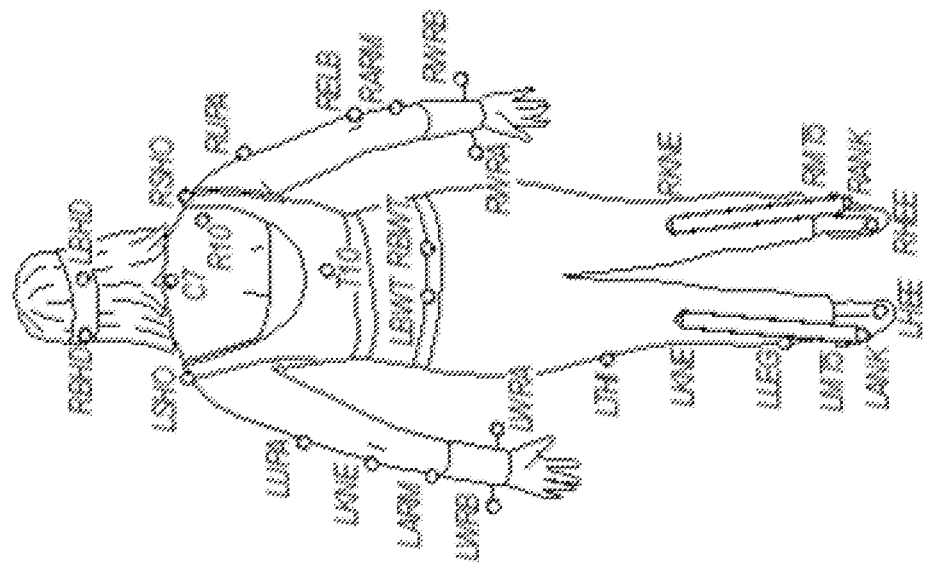
FIG. 6B illustrates left and right knee angles as can be seen from a rear view of a human body.
Figure 6A:
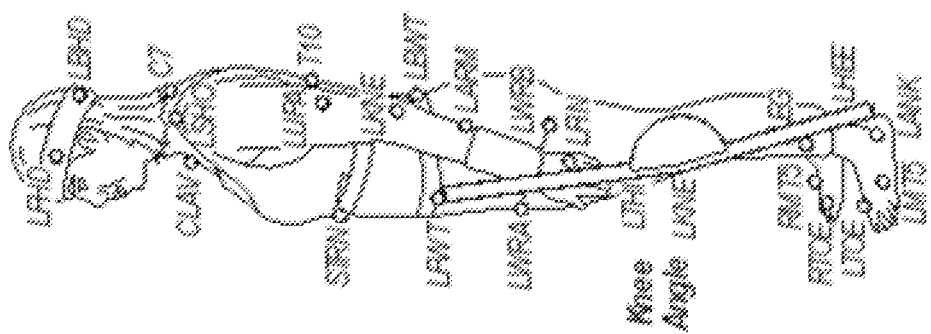
FIG. 6A illustrates left knee angle as can be seen from a left-side view of a human body.
Figure 6C:
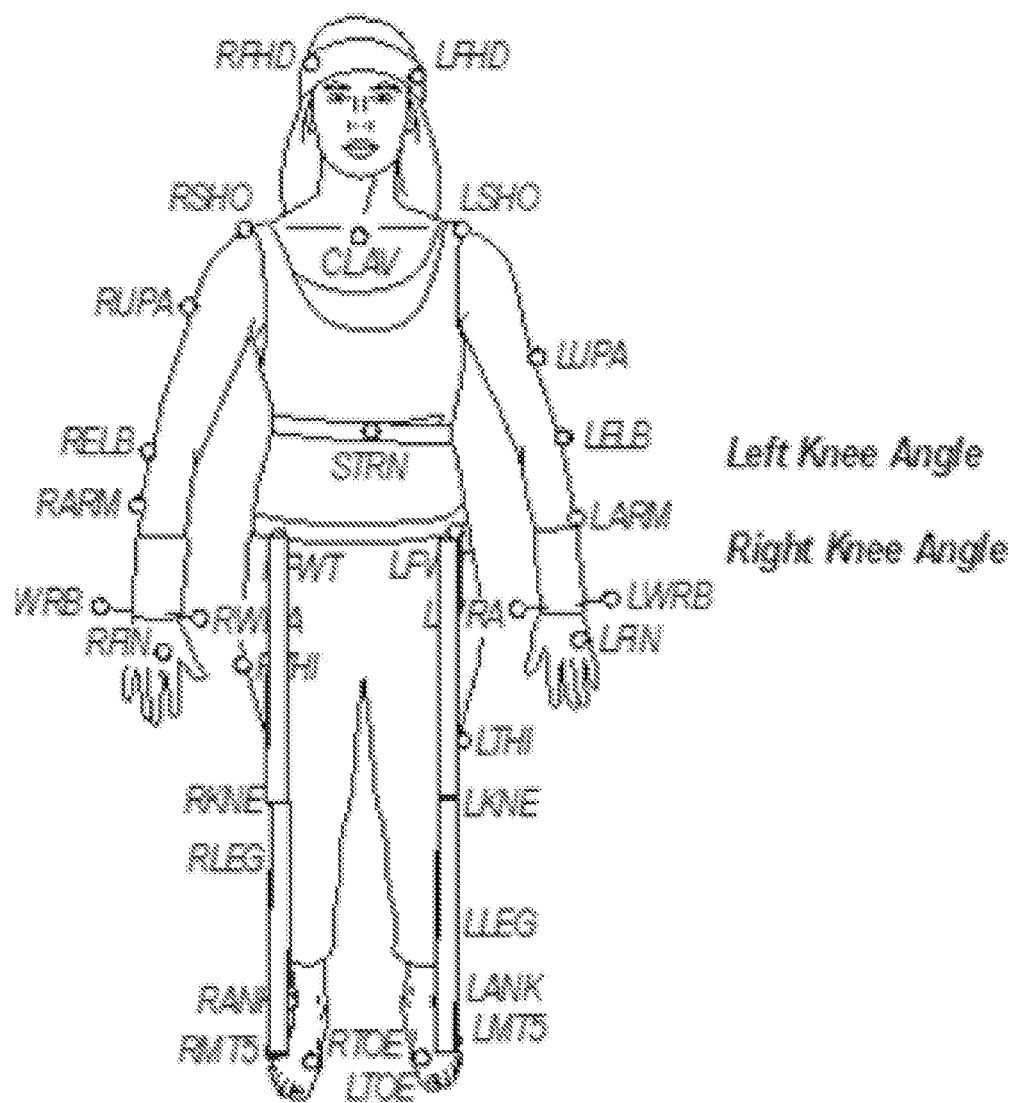
FIG. 6C illustrates left and right knee angles as can be seen from a frontal view of a human body.

FIGS. 5A-C illustrate how the left and right hip angle of a subject can be readily monitored. The left hip angle may be defined by LFWT, LBWT, and LKNE, while the right hip angle may be defined by RFWT, RBWT, and RKNE. FIGS. 6A-C illustrate how the left and right knee angle of a subject can be readily monitored. The left knee angle may be defined by LFWT, LKNE, and LHEE, while the right knee angle may be defined by RFWT, RKNE, and RHEE. Because these markers can be independently monitored, a computing device can discover variations in an angular feature, as well as variations in the relationship between multiple angular features. For example, a computing device may monitor movement data to detect variations in left hip angle, right hip angle, and/or the relationship between left and right hip angle.

Values for these angular features can be determined by assessing the static posture of the subject or the dynamic posture of the subject during a movement pattern. Diagnoses are generally rendered by comparing one or more of the values to an angular feature set known to represent confirmed cases of a disorder. Here, for example, pregnancy can be affirmatively diagnosed based on at least one of the angular features shown in FIGS. 3A-D, FIGS. 4A-B, FIGS. 5A-C, and FIGS. 6A-C. Diagnostic accuracy may increase if the values for multiple angular features (e.g., the upper/lower pelvic angle and the left/right hip angle) are compared to the angular feature set.

Because the values for the angular feature(s) are created based on movement data generated by motion capture technology during a motion capture session, diagnoses can also be rendered based on how the values change over time and with respect to one another. Thus, diagnoses are not limited to static values that represent subject posture during a single moment in time. Instead, diagnoses can be based on dynamic values that represent subject posture as it changes over a time interval (e.g., during performance of a known activity).

Figure 7:
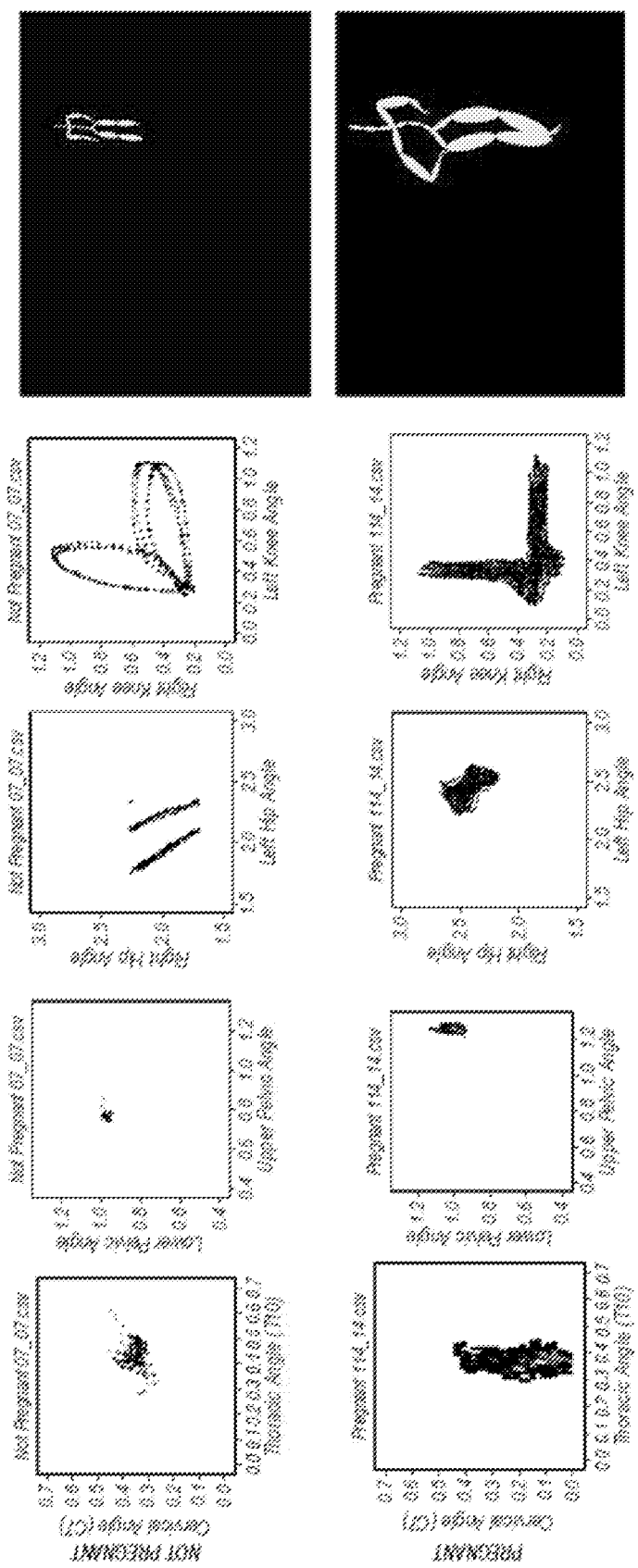
FIG. 7 depicts several two-dimensional (2D) digital characterizations of movement data.

FIG. 7 depicts several two-dimensional (2D) digital characterizations of movement data. Each digital characterization includes a pattern that is indicative of subject movement over a specified period of time, and thus can be used investigate the dynamic relationship between different parts of the subject's body. Moreover, the digital characterizations allow an individual to visually observe how values for certain angular features compare to historical patterns associated with the same subject or patterns associated with other subjects. The individual may the subject under examination or a medical professional responsible for diagnosing and/or treating the subject under examination.

Although digital characterizations are presented in chart form, those skilled in the art will recognize that these patterns could also be summarized in numerical form. For example, any appropriate statistical similarity measure could be used to specify the similarity between at least one value for an angular feature and the values of an angular feature set known to be associated with a certain disorder.

The digital characterizations can be used to illustrate how values change over time for a given angular feature, unlike conventional diagnostic methodologies that are based on a single static representation of posture. The digital characterizations also enable multiple angular features to be compared with one another. For example, a medical professional (e.g., a neurologist, podiatrist, or physiatrist) may compare changes in thoracic angle to changes in upper pelvic angle in order to determine the likelihood of pregnancy. The digital characterizations provide a more holistic picture of subject movement that is quantifiable in nature.

Medical professionals may use the movement data to gain a better sense of the symptoms that are exhibited by a subject. In fact, the digital characterizations may be used to identify symptoms that are largely or entirely imperceptible to the naked eye. For example, a medical professional may not be able to identify small variations in lower pelvic angle or upper pelvic angle by simply observing a subject.

However, rendering accurate diagnoses may still be difficult due to inconsistent symptoms and varied symptom intensities across a pool of subjects. For example, subjects suffering from the same disorder (e.g., Parkinson's disease) may experience different (i.e., heterogeneous) symptoms or similar (i.e., homogeneous) symptoms of differing intensity. Although monitoring higher-order angular features defined by the markers shown in FIGS. 1A-D and FIGS. 2A-D permits more granular analysis of subject movement, these issues will affect the accuracy of diagnoses regardless.

Accordingly, the technology introduced here could also be used in several other manners. For example, the values associated with one or more angular features may indicate that a certain disorder can be eliminated as the source of symptoms experienced by a subject. That is, an analytics platform (e.g., analytics platform 1000 of FIG. 10) may eliminate a certain disorder (e.g., pregnancy) as a potential diagnosis rather than affirmatively diagnose the subject with the certain disorder.

As another example, the analytics platform may generate confidence scores that can be used by a medical professional (e.g., a neurologist, podiatrist, or physiatrist) to assist in diagnosing or treating a subject. As noted above, rendering accurate diagnoses can be difficult due to inconsistent symptoms and varied symptom intensities across subjects. For instance, both Parkinson's disease and certain traumas (e.g., an ankle sprain) may affect the gait of a subject. However, the analytics platform can be configured to determine which disorders is most likely to be the source of a symptom experienced by a subject based on the similarity between the movement data of the subject and movement data corresponding to confirmed cases of each disorder under consideration.

In such embodiments, the analytics platform can filter disorders as candidates based on the type of movement detected. For example, if the analytics platform detects an abnormal gait, the analytics platform may eliminate certain disorders (e.g., upper body injuries affecting the head, shoulders, arms, etc.) as candidate disorders. The analytics platform can then generate confidence scores that indicate the likelihood the subject suffers from each disorder (e.g., 20% likelihood of Parkinson's disease, 30% likelihood of a traumatic injury, etc.). Although confidence scores will typically be inappropriate for affirmatively diagnosing disorders, the confidence scores may be useful to medical professionals in identifying the most appropriate medical test or treatment. For example, a medical professional may request neurological tests be performed if there is a significant likelihood of Parkinson's disease. As another example, the medical professional may recommend the subject apply ice and schedule another appointment if there is a significant likelihood of a traumatic injury. In some embodiments significance thresholds are automatically defined by the analytics platform (e.g., by prompting a medical professional to perform additional tests if the likelihood exceeds a certain percentage such as 50%, 66%, 75%, or 90%), while in other embodiments significance thresholds are manually defined by a medical professional.

Several use cases illustrate the flexibility of the technology.

A first subject undergoes knee replacement surgery. Movement of the subject is tracked during several motion capture sessions that occur over the course of several weeks. The analytics platform can parse the movement data corresponding to each motion capture session to determine whether the knee is improving over time, responding to physical therapy, negatively affecting other aspects of gait, etc.

A second subject experiences lower back pain and visits a medical professional. Lower back pain often prompts unnecessary surgeries because symptoms are limited (e.g., lower back pain may be the only symptom) and treatment progression is difficult to monitor. However, the analytics platform may be able to parse movement data and properly stratify the second subject into an appropriate treatment program at low cost since invasive medical tests are not required.

FIG. 8 depicts a flow diagram of a process 800 for performing an angular feature search. Initially, movement data is imported by an analytics platform (e.g., analytics platform 1000 of FIG. 10) (step 801). For example, 4-second walk segments from 10 different subjects may be imported by the analytics platform. In some embodiments the movement data is retrieved by the analytics platform from a network-accessible database, while in other embodiments the movement data is uploaded directly to the analytics platform (e.g., by a medical professional responsible for overseeing the subjects).

The resolution of each segment depends on the type of motion capture technology used to track the movement of the subjects. Thus, the resolution of each segment may vary based on the number of markers affixed to each subject. For example, if 41 markers are affixed to each subject, then each segment may have approximately 500 sampling points spread out over the 4-second duration at which the location of all 41 markers is determined.

In some embodiments the location of each marker is periodically monitored during the performance of an activity (e.g., every 0.1, 0.25, or 0.5 seconds), while in other embodiments the location of each marker is continually monitored during the performance of the activity. Continual monitoring generally ensures that each marker can be seamlessly tracked throughout a session without disruption. Periodic monitoring, meanwhile, may require that an analytics platform infer where a marker is located between adjacent sampling points.

A subject may be prompted to move in a variety of different ways to see which body parts, if any, are functioning differently than in the past. For example, the subject may be asked to crouch, walk, run, jump, bend over, etc. In some embodiments, the subject is asked to repeat the activity several times in quick succession. Such action may help ensure that the subject is not knowingly modifying their behavior in order to reduce the impact of pain, which will ultimately affect any diagnoses rendered by the analytics platform.

The analytics platform can then identify one or more angular features defined by the markers (step 802). For example, in some embodiments the analytics platform calculates all possible angles between the markers. If 41 markers are affixed to each of 10 subjects, then there will be approximately 66,000 different angles per sampling point.

Statistical model(s) can then be used to identify the angular feature(s) that may be useful for subject stratification. For example, the analytics platform may run analysis of variance (ANOVA) on the identified angular feature(s) (step 803) and determine the F-statistic for each identified angular feature (step 804). If the F-statistic is high, then between-subject variability (also referred to as "explained variance") is higher than within-subject variability (also referred to as "unexplained variance"). Said another way, the F-statistic will be large if the between-group variability is large relative to the within-group variability, which is unlikely to happen if the statistical means of the different subjects have the same value. Angular features that have high F-values are often more beneficial in stratifying subjects, and thus can be identified as candidates for disorder metrics (step 805).

FIG. 9 depicts a flow diagram of a process 900 for rendering a diagnosis of a disorder. Such a process could employ, for example, aspects of gait phenotyping to detect the presence of spinal diseases and render an affirmative diagnosis. However, as noted above, similar processes could also be used to eliminate a certain disorder as the source of symptoms experienced by a subject, generate confidence scores that can be used to aid in diagnosing or treating a subject, monitor disorder progression due to treatment or lack thereof, etc. For example, the process 900 may enable medical professionals to more precisely and accurately phenotype progression of a disease that affects movement and posture. As another example, the process 900 could be used to improve patient stratification for more tailored heath care.

Movement data is initially acquired by an analytics platform (e.g., analytics platform 1000 of FIG. 10) (step 901). Some embodiments may use active markers or passive markers to generate the movement data representing subject movement, while other embodiments may use inertial sensors or virtual marker technology. Some embodiments may use multiple types of marker technology (e.g., active markers and inertial sensors). The process 900 is generally source-agnostic so long as movement data generated by motion capture technology is made available to the analytics platform.

The analytics platform can then parse the movement data and identify one or more angular features (step 902). An angular feature defines the angular relationship between a certain set of markers tracked by the motion capture technology. Accordingly, the analytics platform may examine the movement data to determine which markers have values associated with them. Examples of dynamic, higher-order angular features include cervical angle variability, thoracic angle variability, upper/lower pelvic angle variability, left/right hip angle variability, and left/right knee angle variability, as well as synchronicity between any pair of angular features.

The analytics platform can then analyze one or more values associated with the angular feature(s) (step 903). More specifically, the analytics platform can determine whether the values associated with any of the angular feature(s) are indicative of the presence of a disorder. Some disorders may be detected by monitoring a single angular feature, while other disorders may require that multiple angular features be monitored. Although a single angular feature may be of limited use in isolation, multiple angular features may be useful in detecting the presence of disorders when considered collectively. Monitoring multiple angular features in a dynamic manner may provide an accurate indication of postural abnormality with respect to either the subject being tested or a pool of previously tested subjects. For example, the analytics platform may detect small changes in left hip angle and right hip angle that together cause a large change in the synchronicity between the left and right hip angle.

In response to analyzing the value(s) associated with the angular feature(s), the analytics platform can render a diagnosis of a disorder if appropriate (step 904). For example, the analytics module may affirmatively diagnose a disorder if the value(s) of the angular feature(s) corresponding to that disorder are discovered to exceed a certain threshold. As another example, the analytics module may affirmatively diagnose the disorder if the value(s) of the angular feature(s) are statistically similar to those of other subjects known to suffer from the disorder.

The value of an angular feature may be represented as a single number or a collection of numbers that form a pattern, as shown in FIG. 7. Therefore, the analytics platform may perform comparisons of individual values or patterns representing the values of an angular feature over a period of time. Note that the analytics platform may also simply specify that the value(s) of the angular feature(s) are not indicative of any disorders.

Various machine learning algorithms and techniques could be employed by the analytics platform, including Naïve Bayes Classifier algorithms, K Means Clustering algorithms, Support Vector Machine algorithms, linear regression, logic regression, artificial neural networks, etc. These machine learning algorithms/techniques may be chosen based on application (e.g., supervised or unsupervised learning) and optimized based on whether a medical professional has confirmed or denied a candidate diagnosis proposed by the analytics platform. For example, an analytics platform may apply supervised machine learning algorithms to improve its ability to recognize/diagnose movement disorders based on its examination of location data indicating where one or more markers affixed to a human body are located over a period of time. The analytics platform may be further trained using the location data (in addition to, or instead of, angular feature sets known to represent confirmed cases of different movement disorders) to create/improve models for detecting the presence of movement disorders.

Unless contrary to physical possibility, it is envisioned that the steps described above may be performed in various sequences and combinations. For example, the analytics platform may perform at least some of these steps multiple times over a certain time interval in order to track the effectiveness of an administered treatment or an ongoing therapy program, the progression of degenerative disorders, etc.

Other steps may also be included in some embodiments. For example, dynamic, higher-order angular features could also be used to diagnose and/or stratify individuals using gait-based authentication. In such embodiments, the analytics platform could automatically track disease progression for one or more individuals who consistently inhabit an environment (e.g. a network-connected nursing home, community center, or hospital). The analytics platform could then identify specific individuals by comparing recently recorded gait samples to previously recorded gait samples.

Processing Systems

Figure 10:
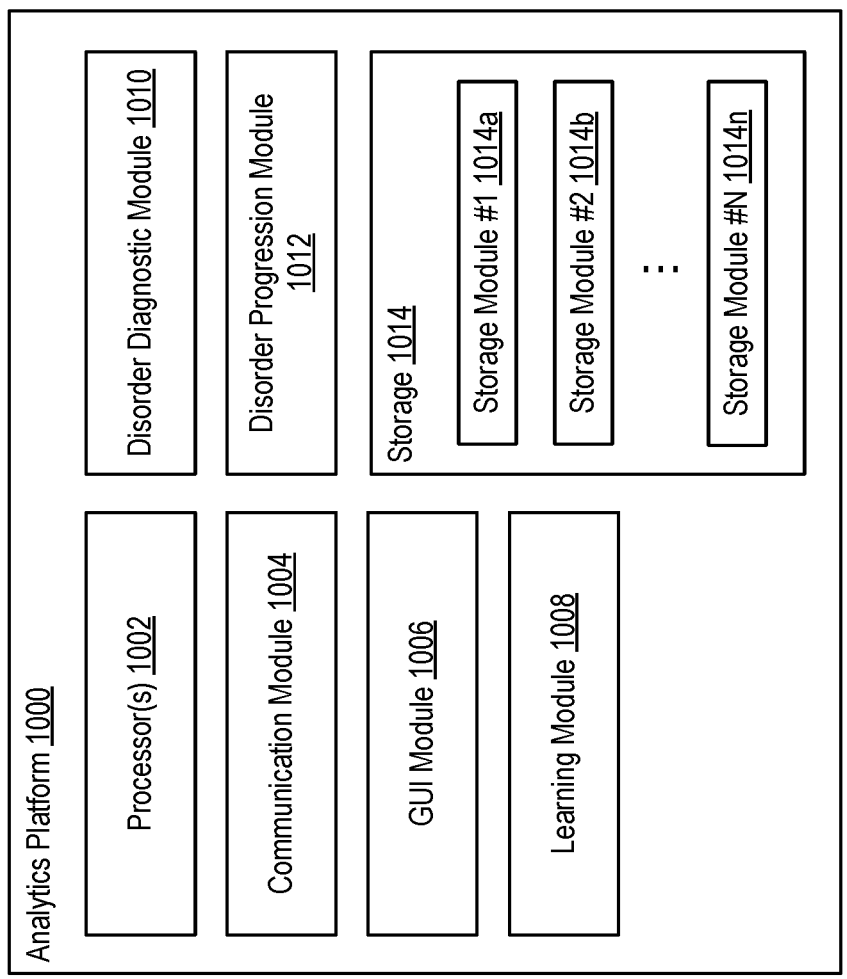
FIG. 10 is a block diagram of an analytics platform configured to acquire, parse, and/or analyze movement data generated by motion capture technology.

FIG. 10 is a block diagram of an analytics platform 1000 configured to acquire, parse, and/or analyze movement data generated by motion capture technology. The analytics platform 1000 can include one or more processors 1002, a communication module 1004, a graphical user interface (GUI) module 1006, a learning module 1008, a disorder diagnostic module 1010, a disorder progression module 1012, and storage 1014. Other embodiments of the analytics platform 1000 may include some or all of these components, as well as other components not shown here.

The processor(s) 1002 can execute the modules from instructions stored in storage 1014, which can be any device or mechanism capable of storing information. Communication module 1004 may manage communication between components of the analytics platform 1000 and/or between the analytics platform 1000 and another computing device. For example, the communication module 1004 may receive movement data that is wirelessly uploaded by a motion capture technology (e.g., one or more network-connected inertial sensors). As another example, the communication module 1004 may transmit notifications of diagnoses or the movement data itself to a computing device associated with a subject or a medical professional for further review. The movement data received by the communication module 1004 can be stored in storage 1014, a remote storage accessible to the analytics platform 1000, or any combination thereof. In some embodiments, the storage 1014 includes individual storage modules 1014a-c corresponding to different subjects, examination sessions, disorders, etc. For example, the values of an angular feature and/or movement data can be stored in a subject profile that represents a historical record of angular feature values associated with activities performed by a subject over an interval of time.

The GUI module 1006 can generate an interface that allows a user (e.g., a subject or a medical professional) to interact with the analytics platform 1000. The interface may be presented by a web browser, desktop application, mobile application, or over-the-top (OTT) application. Accordingly, the interface may be accessible via a mobile phone, tablet computer, personal computer, game console, wearable electronic device (e.g., a watch or fitness tracker), network-connected ("smart") devices, virtual/augmented reality systems, etc.

The disorder diagnostic module 1010 can parse the movement data associated with a subject in order to determine whether the values associated with any angular feature(s) are indicative of the presence of a disorder. More specifically, the disorder diagnostic module 1010 can simultaneously or sequentially monitor the values of multiple angular features in a dynamic manner to identify postural abnormalities. In some embodiments the disorder diagnostic module 1010 diagnoses a disorder if the values of an angular feature corresponding to the disorder are discovered to exceed a certain threshold, while in other embodiments the disorder diagnostic module 1010 diagnoses the disorder if the values of the angular feature are statistically similar to those of other subjects known to suffer from the disorder. For example, if the disorder diagnostic module 1010 determines that an angular feature corresponding to a subject is statistically similar to angular features corresponding to subjects known to be afflicted with Parkinson's disease, then the disorder diagnostic module 1010 may generate a notification that specifies the subject is likely to have Parkinson's disease. Those skilled in the art will recognize that such diagnoses will typically represent proposed diagnoses that must be confirmed by a medical professional, who may order additional medical tests, examine other angular features, etc.

The disorder progression module 1012 can parse the movement data associated with a subject in order to monitor the progression of a disorder. Generally, the disorder progression module 1012 will extract the values of an angular feature from the movement data, and then compare the values to one or more sets of values that were previously generated for the same subject. Accordingly, the disorder progression module 1012 may analyze the values of certain angular feature(s) multiple times over a period of time in order to track the effectiveness of an administered treatment or an ongoing therapy program, the progression of degenerative disorders, etc.

Some embodiments include a learning module 1008 that adds, modifies, or deletes characteristics of angular features from an angular feature set based on the response to diagnoses rendered by the disorder diagnostic module 1010, measures of progression generated by the disorder progression module 1012, etc. For example, the learning module 1008 may discover that some angular features are more relevant than others in diagnosing a disorder. In such embodiments, the learning module 1008 can assign different weights to the angular features based on their importance in rendered an accurate diagnosis. Angular features that are highly relevant for diagnostic purposes will generally be assigned a high weight.

The learning module 1008 can employ various machine learning algorithms and techniques to improve the effectiveness of the disorder diagnostic module 1010 and/or the disorder progression module 1012. Examples of machine learning algorithms/techniques include Naïve Bayes Classifier algorithms, K Means Clustering algorithms, Support Vector Machine algorithms, linear regression, logic regression, and artificial neural networks. As such, the learning module 1008 can ensure that disorders are properly characterized by the appropriate angular feature(s) as more is learned about each disorder. For example, the learning module 1008 may dissociate a feature from a disorder upon discovering that the feature is not indicative of the disorder. As another example, the learning module 1008 may associate a feature with a disorder upon discovering that the feature is indicative of the disorder. By continually monitoring whether diagnoses proposed by the disorder diagnostic module 1010 have been confirmed, the learning module 1008 may ensure that the appropriate links between angular features and disorders are maintained.

Figure 11:
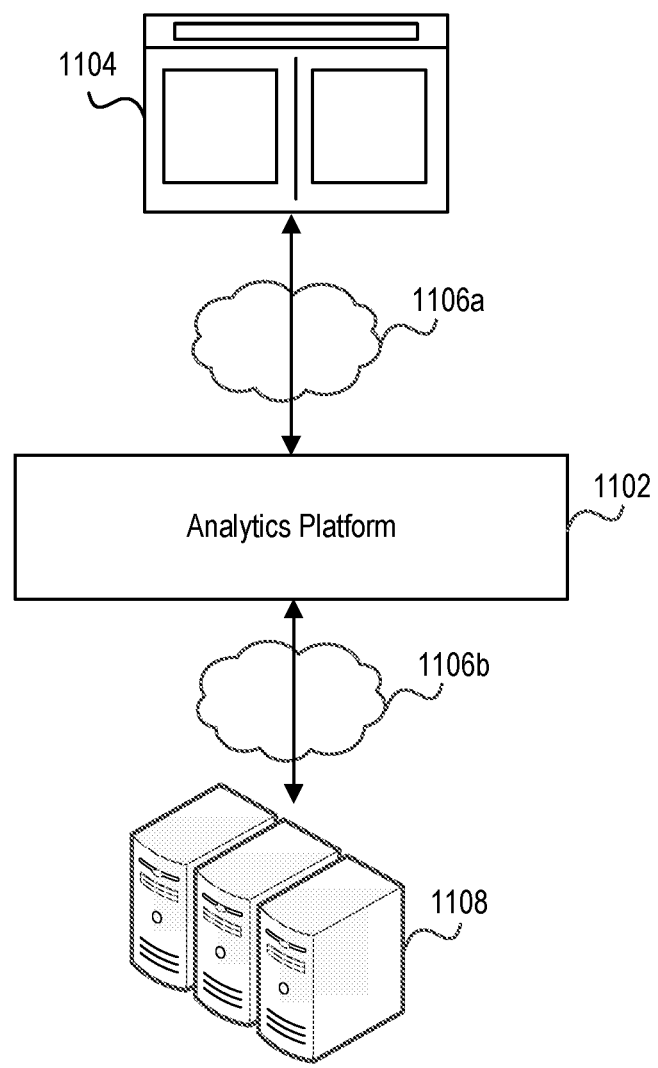
FIG. 11 illustrates a network environment that includes an analytics platform.

FIG. 11 illustrates a network environment 1100 that includes an analytics platform 1102. The analytics platform 1102 could be, for example, analytics platform 1000 of FIG. 10. Individuals can interface with the analytics platform 1102 via an interface 1104. The analytics platform 1102 may be responsible for parsing movement data to detect values associated with markers affixed to a human body, determining the value of an angular feature defined by at least two markers, monitoring changes in the value of the angular feature, estimate a health state based on the value(s) of the angular feature, etc. The analytics platform 1102 may also be responsible for creating interfaces through which the individual can view movement data, review proposed diagnoses, manage preferences, etc.

Movement data could pertain to activities involving the individual accessing the interface 1104 or some other person. For example, in some embodiments the interface 1104 enables a person whose health state is being monitored to view their own movement data (or analysis of such data), while in other embodiments the interface enables an individual to view movement data (or analysis of such data) associated with some other person. The individual may be a medical professional responsible for monitoring the health state of the other person. Examples of medical professionals include physicians, nurses, etc. Some interfaces are configured to facilitate interactions between subjects and medical professionals, while other interfaces are configured to serve as informative dashboards for subjects.

As noted above, the analytics platform 1102 may reside in a network environment 1100. Thus, the analytics platform 1102 may be connected to one or more networks 1106*a-b*. The network(s) 1106*a-b* can include personal area networks (PANs), local area networks (LANs), wide area networks (WANs), metropolitan area networks (MANs), cellular networks, the Internet, etc. Additionally or alternatively, the analytics platform 1102 can be communicatively coupled to computing device(s) over a short-range communication protocol, such as Bluetooth® or Near Field Communication (NFC).

The interface 1104 is preferably accessible via a web browser, desktop application, mobile application, or OTT application. Accordingly, the interface 1104 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the analytics platform 1102 are hosted locally. That is, the analytics platform 1102 may reside on the computing device used to access the interface 1104. For example, the analytics platform 1102 may be embodied as a mobile application executing on a mobile phone. Other embodiments of the analytics platform 1102 are executed by a cloud computing service operated by Amazon Web Services® (AWS), Google Cloud Platform™, Microsoft Azure®, or a similar technology. In such embodiments, the analytics platform 1102 may reside on a host computer server that is communicatively coupled to one or more content computer servers 1108. The content computer server(s) 1108 can include movement data generated by motion capture technology, angular feature sets corresponding to different disorders, user information (e.g., profiles, credentials, and health-related information such as age, health diagnoses, etc.), and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., movement data, angular feature sets, or processing operations) to be downloaded at a single point in time or on a periodic basis (e.g., weekly, daily, or hourly).

Figure 12:
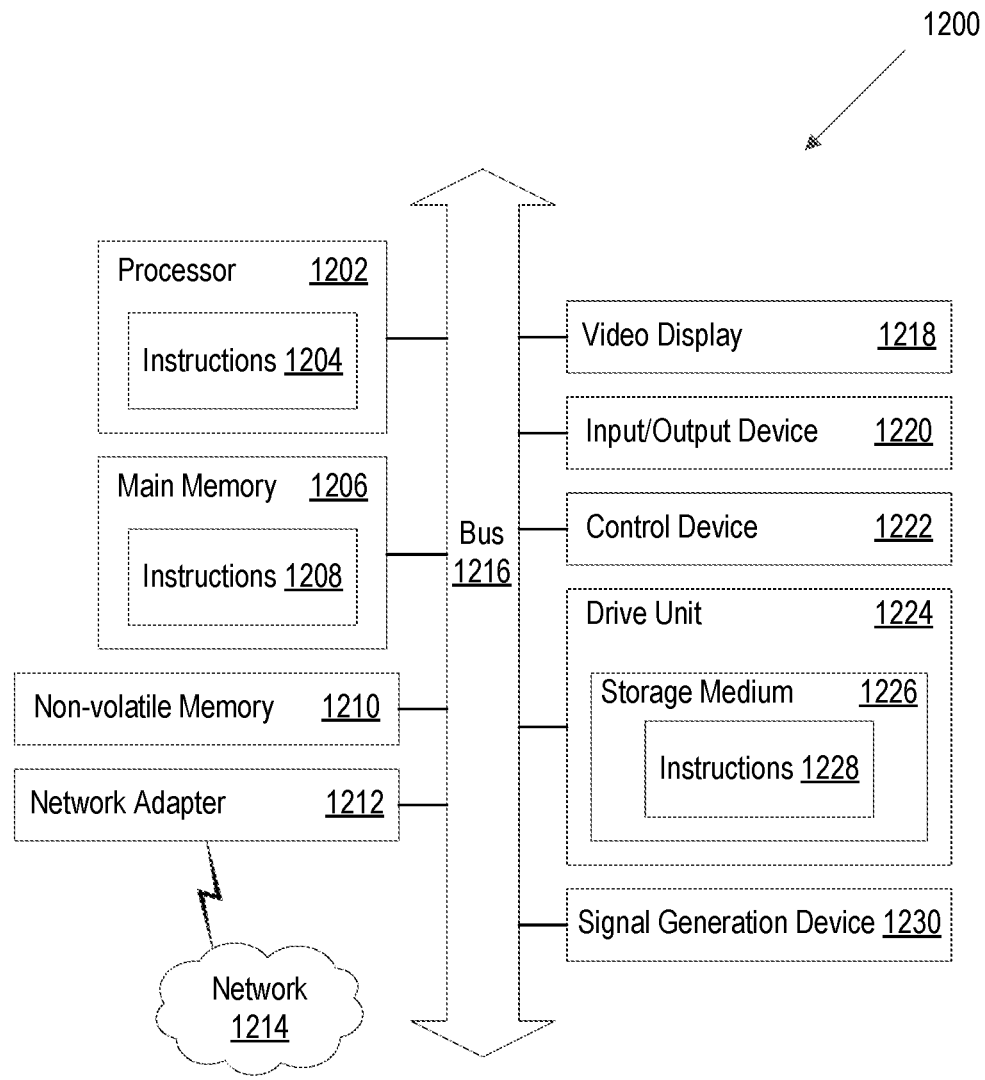
FIG. 12 is a block diagram illustrating an example of a processing system in which at least some operations described herein can be implemented.

FIG. 12 is a block diagram illustrating an example of a processing system 1200 in which at least some operations described herein can be implemented. For example, some components of the processing system 1200 may be hosted on a computing device that includes an analytics platform (e.g., analytics platform 1000 of FIG. 10).

The processing system may include one or more central processing units ("processors") 1202, main memory 1206, non-volatile memory 1210, network adapter 1212 (e.g., network interfaces), video display 1218, input/output devices 1220, control device 1222 (e.g., keyboard and pointing devices), drive unit 1224 including a storage medium 1226, and signal generation device 1230 that are communicatively connected to a bus 1216. The bus 1216 is illustrated as an abstraction that represents one or more physical buses and/or point-to-point connections that are connected by appropriate bridges, adapters, or controllers. The bus 1216, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1200 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1200.

While the main memory 1206, non-volatile memory 1210, and storage medium 1226 (also called a "machine-readable medium") are shown to be a single medium, the term "machine-readable medium" and "storage medium" should be taken to include a single medium or multiple media (e.g., a centralized or distributed database, and/or associated caches and servers) that store one or more sets of instructions 1228. The term "machine-readable medium" and "storage medium" shall also be taken to include any medium that is capable of storing, encoding, or carrying a set of instructions for execution by the processing system 1200.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1204, 1208, 1228) set at various times in various memory and storage devices in a computing device. When read and executed by the one or more processors 1202, the instruction(s) cause the processing system 1200 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1210, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1212 enables the processing system 1200 to mediate data in a network 1214 with an entity that is external to the processing system 1200 through any communication protocol supported by the processing system 1200 and the external entity. The network adapter 1212 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1212 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A non-transitory computer-readable medium with instructions stored thereon that, when executed by a processor, cause the processor to perform operations comprising:
acquiring movement data generated by monitoring movement of multiple markers that are adapted for arrangement on a human body of a subject while the human body performs an activity;
identifying an angular feature defined by the multiple markers,
wherein the multiple markers include (i) a marker that is representative of a pivot point and (ii) a pair of markers that represent ends of branches extending from the pivot point, and
wherein the angular feature is defined by a spatial relationship between the pair of markers with respect to the marker;
computing a first set of values of the angular feature during the performance of the activity by analyzing the movement data; and
detecting a presence of a disorder by:
comparing the first set of values of the angular feature to an angular feature set that includes a second set of values of the angular feature,
wherein the second set of values corresponds to a performance of the activity by a person other than the subject who is known to represent a confirmed case of the disorder, and
producing, based on said comparing, an output that indicates a likelihood that the human body is affected by the disorder.

2. The non-transitory computer-readable medium of claim 1, wherein the operations further comprise:
generating a similarity measure that represents statistical similarity between the first set of values and the second set of values of the angular feature; and
rendering an affirmative diagnosis of the disorder responsive to a determination that the similarity measure exceeds a certain threshold.

3. The non-transitory computer-readable medium of claim 1, wherein the operations further comprise:
generating a similarity measure that represents statistical similarity between the first set of values and the second set of values of the angular feature; and
rendering a negative diagnosis of the disorder responsive to a determination that the similar measure does not exceed a certain threshold.

4. The non-transitory computer-readable medium of claim 1, wherein the operations further comprise:
retrieving historical values of the angular feature from a database,
wherein the historical values correspond to at least one prior performance of the activity by the human body;
comparing the first set of values of the angular feature to the historical values of the angular feature; and
estimating a measure for disorder progression based on said comparing.

5. The non-transitory computer-readable medium of claim 1, wherein the operations further comprise:
causing generation of a notification that specifies the likelihood that the human body is affected by the disorder.

6. The non-transitory computer-readable medium of claim 5, wherein the notification is presented to a medical professional responsible for overseeing treatment of the human body under examination.

7. The non-transitory computer-readable medium of claim 1, wherein the operations further comprise:
storing the first set of values of the angular feature in a subject profile representing a historical record of angular feature values associated with performances of the activity by the human body over an interval of time.

8. The non-transitory computer-readable medium of claim 1, wherein a location of each marker of the multiple markers is periodically monitored while the human body performs the activity.

9. The non-transitory computer-readable medium of claim 1, wherein a location of each marker of the multiple markers is continually monitored while the human body performs the activity.

10. The non-transitory computer-readable medium of claim 1, wherein each marker of the multiple markers corresponds to a different predetermined location on the human body.

11. A method comprising:
acquiring, by a processor, movement data generated by monitoring movement of multiple markers that are adapted for arrangement on a human body of a subject while the human body performs an activity;
identifying, by the processor, an angular feature defined by the multiple markers,
wherein the multiple markers include (i) a marker that is representative of a pivot point and (ii) a pair of markers that represent ends of branches extending from the pivot point, and
wherein the angular feature is defined by a spatial relationship between the pair of markers with respect to the marker;
computing, by the processor, a first set of values of the angular feature during the performance of the activity by analyzing the movement data;
generating, by the processor, a similarity measure that represents statistical similarity between the first set of values of the angular feature and an angular feature set that includes a second set of values of the angular feature,
wherein the second set of values corresponds to a performance of the activity by a person other than the subject who is known to represent a confirmed case of a disorder; and
determining, by the processor based on the similarity measure, whether to diagnose the human body as having the disorder.

12. The method of claim 11, wherein the human body is diagnosed as having the disorder responsive to a determination that the similarity measure exceeds a threshold.

13. The method of claim 11, wherein the angular feature is one of multiple angular features monitored by the processor, and wherein each of the multiple angular features is defined by a subset of the multiple markers.

14. The method of claim 11, further comprising:
performing analysis of variance on the first set of values of the angular feature.

15. The method of claim 14, wherein the similarity measure is an F-statistic determined through analysis of variance, and wherein said determining is based on a comparison of the F-statistic to a threshold.

16. A computing device comprising:
a memory that includes instructions for monitoring disorder progression over time by analyzing movement during motion capture sessions,
wherein the instructions, when executed by a processor, cause the processor to:

acquire movement data generated in a first motion capture session by monitoring movement of multiple markers that are adapted for arrangement on a human body while the human body performs an activity;

compute values for an angular feature defined by the multiple markers during the performance of the activity based on locations of the multiple markers at corresponding points in time;

retrieve historical values of the angular feature from a database,
 wherein the historical values correspond to at least one prior performance of the activity by the human body in a second motion capture session;

estimate a measure for disorder progression based on a comparison of the values of the angular feature to the historical values of the angular feature; and stratify the human body into a treatment program based on the measure for disorder progression.

17. The computing device of claim 16, wherein the instructions further cause the processor to:

generate a similarity measure by comparing the values of the angular feature to an angular feature set known to represent at least one confirmed case of the disorder; and render a diagnosis of the disorder based on the similarity measure.

18. The computing device of claim 17, wherein when the similarity measure exceeds a threshold, the diagnosis is an affirmative diagnosis of the disorder.

19. The computing device of claim 17, wherein the instructions further cause the processor to:

generate a notification that specifies the diagnosis.

20. A non-transitory computer-readable medium with instructions stored thereon that, when executed by a processor, cause the processor to perform operations comprising:

acquiring movement data that is generated by an inertial measurement unit that is located proximate to a first person while the first person performs an activity;

examining the movement data to infer movements of a first body part and a second body part with respect to a third body part,
 wherein a spatial relationship between the first and second body parts with respect to the third body part defines an angular feature;

computing a first set of values of the angular feature during the performance of the activity by analyzing the movement data; and determining whether to diagnose the first person as having a disorder based on statistical similarity between the first set of values and a second set of values of the angular feature,
 wherein the second set of values corresponds to a performance of the activity by a second person who is known to represent a confirmed case of the disorder.

* * * * *